United States Patent

Yamamori et al.

[11] Patent Number: 5,957,127
[45] Date of Patent: *Sep. 28, 1999

[54] CAPNOMETER

[75] Inventors: Shinji Yamamori; Kohei Ono; Hiroyuki Okada; Michiaki Shishido; Katsumi Nakaichi, all of Tokyo, Japan

[73] Assignee: Nihon Kohden Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/606,302

[22] Filed: Feb. 23, 1996

[30] Foreign Application Priority Data

Feb. 23, 1995 [JP] Japan .................................. 7-035472
Feb. 24, 1995 [JP] Japan .................................. 7-036700

[51] Int. Cl.⁶ ......................................................... A61B 5/08
[52] U.S. Cl. ............................. 128/204.22; 128/205.23; 128/207.14; 600/529; 600/532; 422/84
[58] Field of Search ....................... 128/204.22, 204.23, 128/207.14, 205.23; 600/342, 473, 529, 532; 250/343; 422/84; 436/900; 73/23.3; 356/437, 438; D24/107, 129, 186, 232

[56] References Cited

U.S. PATENT DOCUMENTS

| | | | |
|---|---|---|---|
| 4,067,320 | 1/1978 | Olsson et al. ........................... | 128/2 C |
| 4,653,498 | 3/1987 | New, Jr. et al. ......................... | 128/633 |
| 5,095,913 | 3/1992 | Yelderman et al. ..................... | 128/719 |
| 5,159,934 | 11/1992 | Hoberman ............................... | 600/532 |

FOREIGN PATENT DOCUMENTS

| | | |
|---|---|---|
| 42 01 285 | 7/1992 | Germany . |
| 51-136474 | 11/1976 | Japan . |
| 53-53184 | 5/1978 | Japan . |
| 59-160446 | 9/1984 | Japan . |
| WO 92/02177 | 2/1992 | WIPO . |

Primary Examiner—John G. Weiss
Assistant Examiner—V. Srivastava
Attorney, Agent, or Firm—Sughrue, Mion, Zinn, Macpeak & seas, PLLC

[57] ABSTRACT

A capnometer includes an airway adaptor for letting a respiratory gas pass therethrough, a light source for holding the airway adaptor and irradiating with infrared radiations the respiratory gas passing through the airway adaptor, a detecting portion having an infrared radiation detector for detecting the infrared radiations that have passed through the respiratory gas, and a monitor body for measuring the concentration of respiratory carbon dioxide gas by receiving a signal from the detecting portion, wherein an angle is defined between the channel of the airway adaptor and a display surface of the monitor body.

18 Claims, 7 Drawing Sheets

CAPNOMETER

BACKGROUND OF THE INVENTION

1. Field of the invention

The present invention relates to a detecting portion and an airway adaptor which is fitted to the detecting portion and used for letting pass respiratory gas in, for example, a capnometer for measuring the concentration of carbon dioxide gas contained in expiratory gas.

2. Related art

When the concentration of carbon dioxide gas contained in expiratory gas is measured, the following steps are followed; namely, using an optical detector, for example, PbSe as an infrared radiation detector, causing the respiratory gas to pass through a cylindrical transparent plastic airway adaptor, and irradiating the respiratory gas with infrared radiations from a light source so as to detect, by means of the detector, voltage corresponding to the absorption of light resulting from the expiratory carbon dioxide gas.

FIGS. 12 and 13 are schematic views of an example of a conventional capnometer. In FIGS. 12 and 13, one end 1a of an airway adaptor 1 which is substantially cylindrical and used for letting pass a respiratory gas therethrough is a connection end to be held in a patient's mouth, whereas the other end 1b is an open end communicating with the atmosphere. The intermediate portion of the airway adaptor 1 is square in cross section. Further, coaxial circular windows 1c, 1d are formed in two facing sides of the intermediate portion of the airway adaptor 1, respectively. The intermediate portion of the airway adaptor 1 is detachable from a detecting portion 2.

The detecting portion 2 is in the form of a substantially square pillar, and its intermediate portion is provided with a U-shaped cutaway portion 2e into which the intermediate portion of the airway adaptor 1 is fitted. The facing two sides of the cutaway portion 2e are in contact with the respective windows 1c, 1d of the airway adaptor 1. A light source 3 for emitting infrared radiations is placed on one side of the cutaway portion 2e of the detecting portion 2, whereas a radiation interrupter 5 which is driven to rotate by a motor 4 is situated on the other side. There are also formed a plurality of coaxial light transmitting holes for making light emitted from the light source continuously intermittent in the radiation interrupter 5.

A filter 6 for passing light only having a wavelength to be absorbed by carbon dioxide gas, and a light detector 7 as an infrared radiation detector are disposed in a direction opposite to the light source 3 with respect to the radiation interrupter 5. The light detector 7 is connected via a lead wire 8 to a monitor body 9. In this case, the intermediate portion of the airway adaptor 1 is detachable from the detecting portion 2 via a pair of ball plungers 10 provided in the detecting portion 2.

In the conventional capnometer thus constructed, the light emitted from the light source 3 passes through the window 1c and respiratory gas in the airway adaptor 1, whereas the light emitted through the window 1d is made incident as intermittent light on the optical detector 7 by the radiation interrupter 5 via the filter 6. Thus the light intensity corresponding to the concentration of carbon dioxide gas is detected by the optical detector 7, and an output signal of the optical detector 7 is input to the monitor body 9 before being displayed as the concentration of the carbon dioxide gas.

The aforementioned conventional capnometer employs an expensive PbSe as an infrared radiation detector and because PbSe greatly drifts with temperature variations though response speed is high, light has to be detected while it is made continuously intermittent. For this reason, the conventional capnometer needs the radiation interrupter 5 and the motor 4 for driving the interrupter, so that it tends to become not only large in size but also costly.

Further, a great deal of power is essential to driving the motor 4 to rotate, which results in the necessity of providing a large power supply for the monitor body 9. In addition, there has to be a circuit for demodulating the intermittent detected signal in the monitor body 9 and this also makes it impossible to decrease the size of the monitor body 9. In view of easy-to-use, it has become necessary to use the detecting portion 2 equipped with the airway adaptor 1 separately from the monitor body 9 connected to the former via a lead wire 8.

In a case where the detecting portion 2 equipped with the airway adaptor 1 is used so that it is placed between a mask for covering the mouth of a patient and an air bag fitted to the other end at the time of, for example, ventilation, it will not be possible for a helper to observe the patient's condition such as his complexion simultaneously with the display portion of the concentration of carbon dioxide gas as the detecting portion 2 is separated from the monitor body 9. The trouble is that the helper will have to turn his gaze at all times. Moreover, there has been the possibility that the monitor body 9 may drop or otherwise the lead wire 8 for connecting the detecting portion 2 and the monitor body 9 together may be disconnected during the time a patient is moved on a stretcher since the detecting portion 2 and the monitor body 9 are separated from each other.

Therefore when the concentration of carbon dioxide gas is measured, a helper must supply air while watching the display portion of the monitor body 9. In other words, the monitor body 9 is desired to be integral with the detecting portion 2. However, the problem is that operability will be impaired if the monitor body 9 is fitted with the detecting portion 2 because not only the detecting portion 2 but also the monitor body 9 is large-sized and heavy as set forth above.

The airway adaptor 1 can be made disposable when it is contaminated. However, the airway adaptor 1 has conventionally been fixed to the detecting portion 2 with ball plungers 10. Consequently, the airway adaptor 1 may be set unsatisfactorily without being properly fitted into the cutaway portion 2e of the detecting portion 2. In this case, the light intensity may decrease, which may also deteriorate the S/N precision, thus bringing about an erroneous diagnosis. Since the ball plungers 10 fitted to the detecting portion 2 press the intermediate portion of the airway adaptor 1, the counter force acts in the same direction as that of the optical axis, increases the distance between the light source 3 and the optical detector 7 and decreases the light intensity, so that precision may deteriorate. In order to solve this problem, the rigidity of the detecting portion 2 must be increased.

SUMMARY OF THE INVENTION

In view of the foregoing problems, an object of the present invention is to provide a capnometer having a respiratory airway adaptor detaching mechanism simple in construction in that a detecting portion is made compact and lightweight, and the channel of the airway adaptor is placed so that it intersects the display surface of a monitor body by making the detecting portion integral with the monitor body to ensure that the concentration of carbon dioxide gas is measured with safety while the look of a patient is observed, that the airway adaptor is held securely in position in the detecting portion and that the distance between a light source and a light receiving portion is maintained constant.

In order to accomplish the object above, a capnometer according to the present invention comprises:

an airway adaptor for letting a respiratory gas pass therethrough, a light source for holding the airway adaptor and irradiating with infrared radiations the respiratory gas passing through the airway adaptor, a detecting portion having an infrared radiation detector for detecting the infrared radiations that have passed through the respiratory gas, and a monitor body for measuring the concentration of carbon dioxide gas in the respiratory gas by receiving a signal from the detecting portion wherein the infrared radiation detector is formed with thermal energy detecting elements and wherein the channel of the airway adaptor is situated so that it intersects the display surface of the monitor body.

A capnometer according to the present invention is such that the detecting portion is detachable from the monitor body.

A capnometer according to the present invention is such that the detecting portion is rotatable with respect to the monitor body.

A capnometer according to the present invention further comprises a respiratory airway adaptor detaching mechanism for holding the airway adaptor detachably from the detecting portion, the mechanism including: an elastic member having at least one pawl, the elastic member being integral with the outer periphery of the airway adaptor, and at least one retaining part provided near a cutaway portion into which the airway adaptor formed in the detecting portion is fitted and so arranged in the detecting portion as to retain the elastic member.

In the capnometer thus constructed, the infrared radiation detector is arranged with thermal energy detecting elements. A thermopile (e.g., S60 of Dexter Research Center Inc. of the U.S) is employed as its drifting is lower than that of PbSe as an optical detector that has heretofore been in use. Due to the low drifting of such a thermopile, a radiation interrupter and a motor for driving it to rotate that have heretofore been used can be dispensed with. Consequently, the detecting portion is reducible in size and not only power to be supplied to the motor but also a demodulating circuit necessary for the monitor body can also be dispensed with. Even the monitor body is thus made compact. Moreover, the concentration of carbon dioxide gas is measured with the detecting portion incorporated in the monitor body.

Consequently, it is possible to view the display portion for displaying the concentration of carbon dioxide with the patient's condition and complexion being watched.

In the airway adaptor detaching mechanism thus arranged, the outer peripheries of the pawls of the elastic members each formed on the outer periphery of the airway adaptor mate with the retaining parts formed on both sides of the cutaway portion of the detecting portion when the airway adaptor is fitted into the cutaway portion of the detecting portion and climb over the retaining parts as the elastic members are compressed. When the airway adaptor is inserted into the cutaway portion and when the elastic members climb over the retaining parts, their resilient force restores the elastic members to the original position and retains them in position.

DETAILED DESCRIPTION OF THE PREFERRED EMBODIEMTNS

Referring to the attached drawings, there is shown therein a capnometer embodying the present invention.

Figure 1:
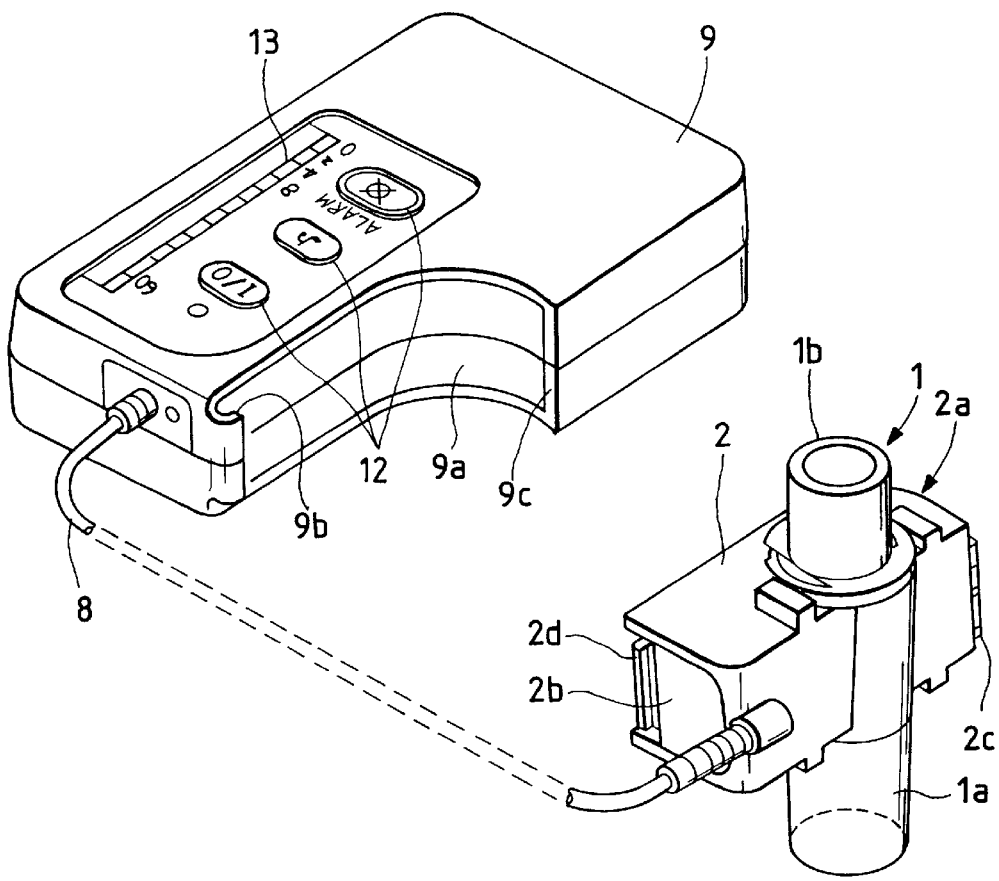
FIG. 1 is a perspective view of a first embodiment of the present invention
Figure 2:
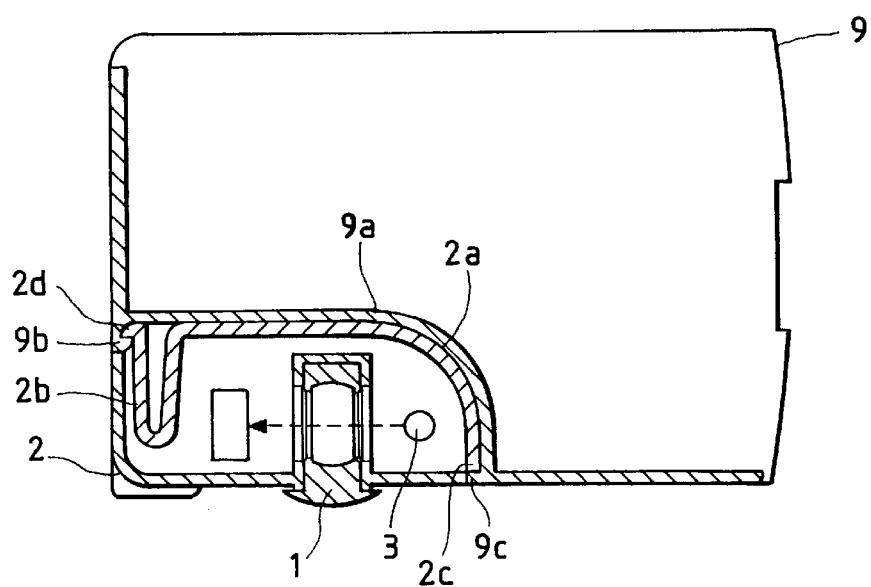
FIG. 2 is a transverse cross sectional view showing the structure of the connection between the detecting portion and the monitor body of FIG. 1.
Figure 13:
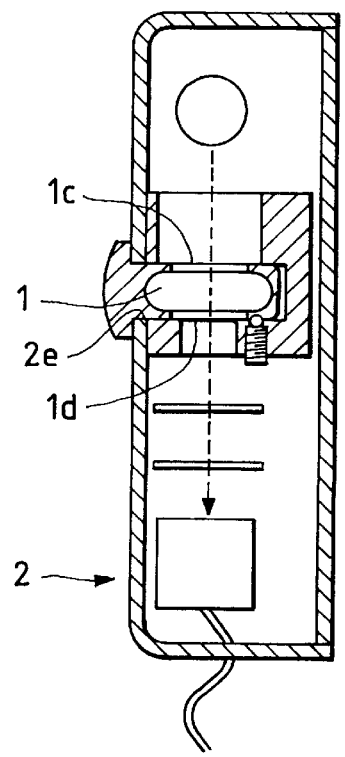
FIG. 13 is a side view showing the construction of the detecting portion of FIG. 12.
Figure 12:
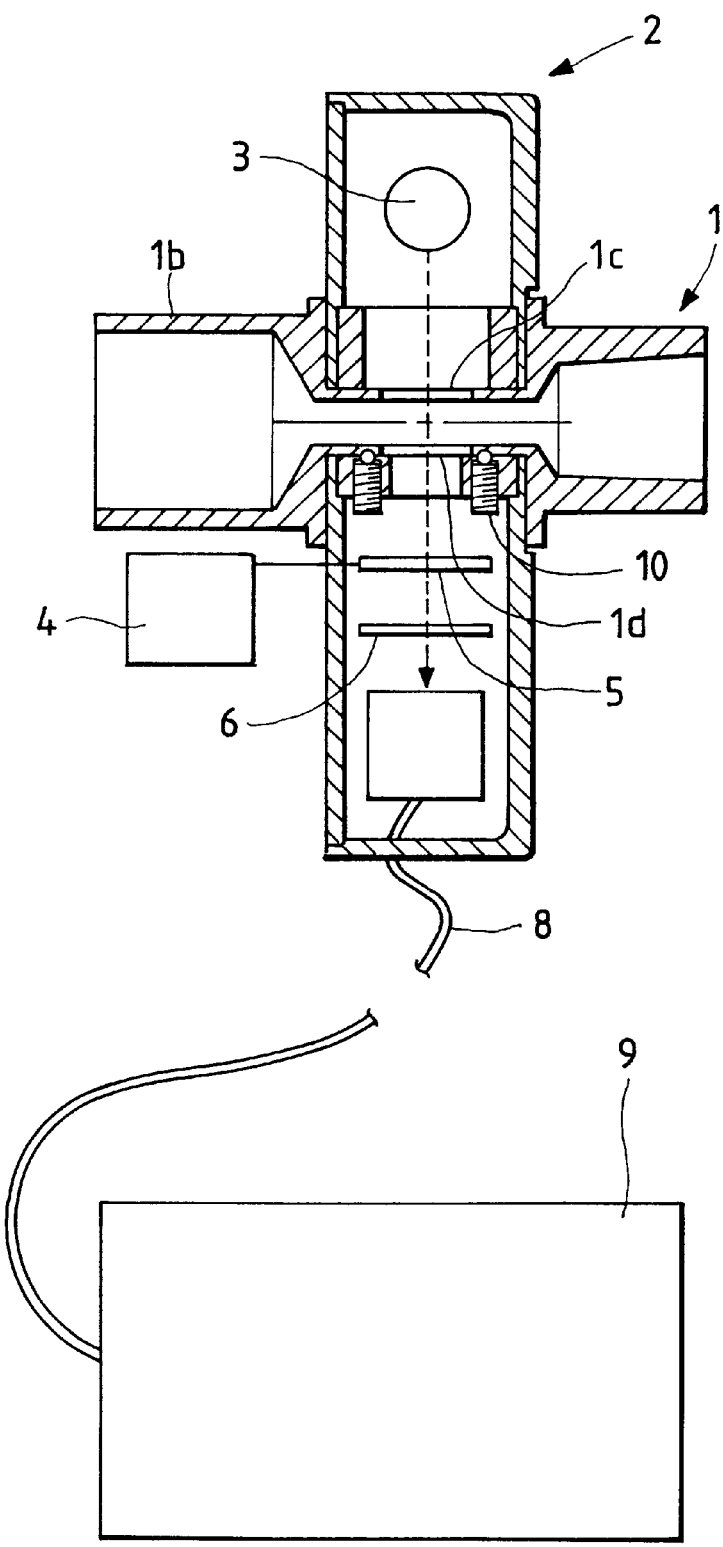
FIG. 12 is a diagram explanatory of the construction of a conventional capnometer.

FIGS. 1 and 2 show an arrangement of an embodiment of a first invention. In FIGS. 1, 2, like reference characters designate like or corresponding parts of the prior art shown in FIGS. 12, 13 and the description thereof will be omitted. This embodiment of the invention is characterized in that a thermopile 11 is used to form an infrared radiation detector installed in a detecting portion 2 and that the channel of an airway adaptor 1 is installed in a direction intersecting a display portion 13 for displaying the concentration of a carbon dioxide gas in a monitor body 9. A substantially arcuate cutaway portion 9a is formed on one side of the monitor body 9, and retaining parts 9b, 9c are each projected from both ends of the cutaway portion 9a. Moreover, operating buttons 12 and the display portion 13 for displaying the concentration of the carbon dioxide gas are provided on the surface of the monitor body 9.

On the other hand, one face 2a of the detecting portion 2 is substantially arcuate so that it mates with the cutaway portion 9a of the monitor body 9, whereas the other face in the longitudinal direction incorporates a U-shaped tongue piece 2b capable of elastic deformation. Further, a stepped portion 2c is formed in the end portion of the one arcuate side face 2a in the longitudinal direction. When the detecting portion 2 is fitted into the cutaway portion 9a by mating the stepped portion 2c with the retaining part 9c of the monitor body 9, the tongue piece 2b undergoes the elastic deformation and its leading end 2d climbs over the retaining part 9b so as to engage therewith. When the leading end 2d of the tongue piece 2b engages with the retaining part 9b in this manner, the channel of the airway adaptor 1 is situated in the direction intersecting the display portion 13. In a case where the detecting portion 2 is removed from the monitor body 9, it is readily removable therefrom by pushing the tongue piece 2b to release the engagement between the leading end 2d and retaining part 9b.

Figure 3:
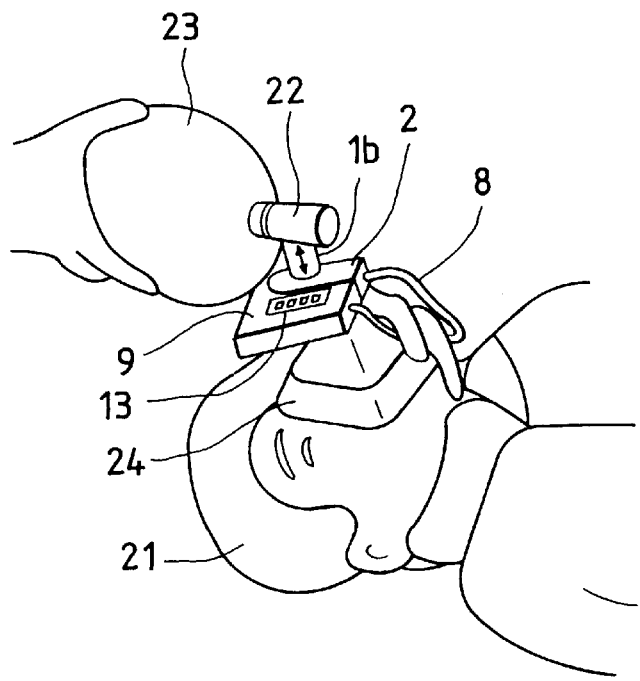
FIG. 3 is a perspective view showing an example of a condition in which the concentration of expiratory carbon dioxide gas of a patient with the detecting portion combined with the monitor body of FIG. 1.
Figure 4:
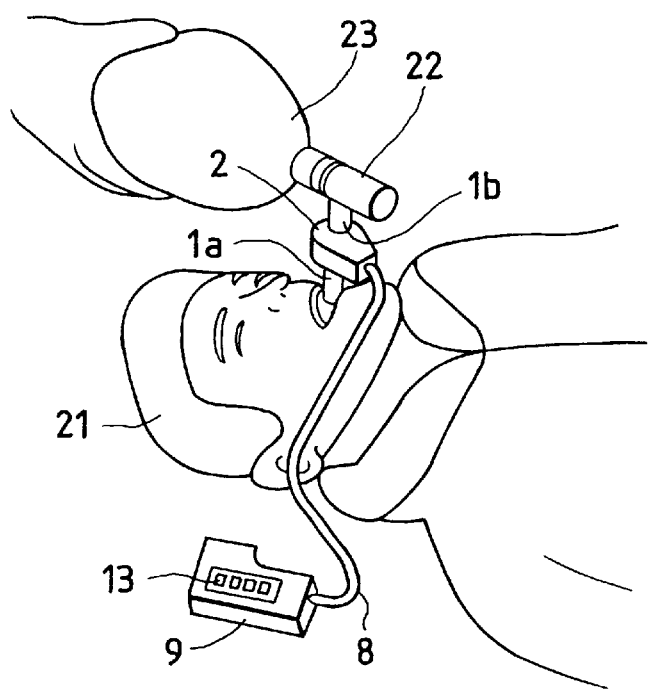
FIG. 4 is a perspective view showing an example of a condition in which the concentration of expiratory carbon dioxide gas of a patient with the detecting portion separated from the monitor body of FIG. 1.

FIGS. 3 and 4 show a condition in which the concentration of expiratory carbon dioxide gas of a patient 21 is measured. In the case of FIG. 3, the detecting portion 2 is fitted to the monitor body 9, and a bag 23 for supplying air is also fitted via a connection pipe 22 to one end 1b of the airway adaptor 1. Further, a mask 24 is fitted to the other end of the airway adaptor 1, and the mask 24 is attached to the face of the patient 21. Further, the air bag 23 is compressed so as to feed air into the lungs of the patient 21. When the air bag 23 is released from being compressed, it is restored to the original stated. The air fed into the lungs of the patient 21 is subjected to gas exchange therein before being discharged via the airway adaptor 1. The concentration of the expiratory carbon dioxide gas is measured in the detecting portion 2.

In the case of FIG. 4, the measurement is made by connecting the other end 1a of the airway adaptor 1 to one end of a tracheal tube inserted into the trachea of the patient 21. In this case, the detecting portion 2 may be removed from the monitor body 9 as shown in FIG. 4.

According to this embodiment of the invention, the thermopile 11 is used as an infrared radiation detector, and the detecting portion 2 is made compact and lightweight by dispensing with an radiation interrupter and a motor for driving the interrupter to rotate. With the monitor body 9 fitted to the detecting portion 2, the concentration of the expiratory carbon dioxide gas can be measured and while the display portion 13 of the monitor body 9 is observed, air can be supplied to ensure that the concentration of carbon dioxide gas is measured with safety while the condition of the patient 21 is observed.

The above configuration of the portion where the detecting portion 2 and the monitor body 9 are fitted to each other and the above structure of the retaining parts 9b, 9c are those that have been shown by way of example according to the aforementioned embodiment of the invention, and the present invention is not limited thereto.

Figure 5:
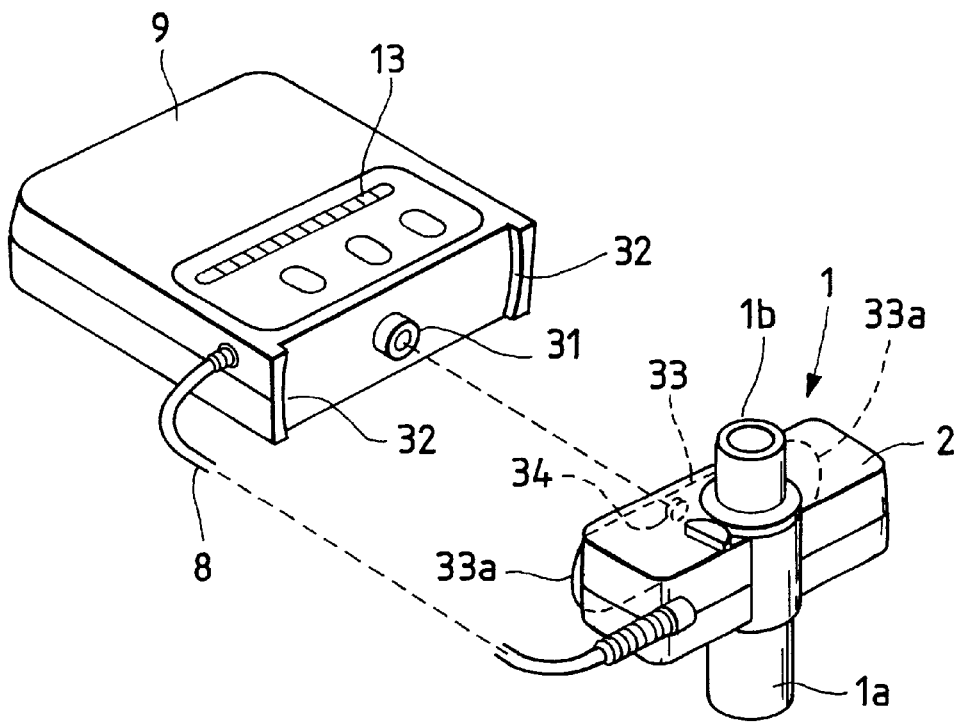
FIG. 5 is a perspective view of a modified embodimnet of the first invention.
Figure 6:
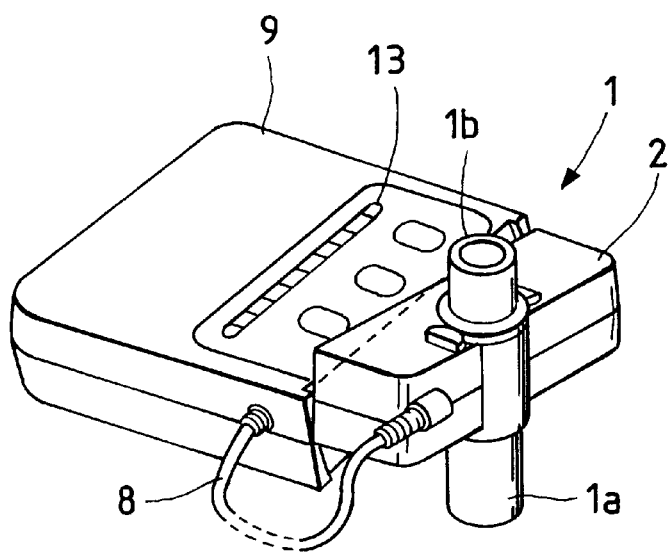
FIG. 6 is a perspective view of a condition in which the detecting portion of FIG. 5 has been turned.

FIGS. 5 and 6 show another embodiment of the invention. According to this embodiment of the invention, the detecting portion 2 is detachably and rotatably fitted via a shaft 31 to the one side of the monitor body 9. The shaft 31 is provided at the center of one side of the monitor body 9, and an integral arcuate guide part 32 is projected at both ends of this side, the curves of the guide parts centering around the shaft 31.

On the other hand, an integral guide plate 33 is formed opposite to the monitor body 9 of the detecting portion 2, and an arcuate part 33a slidably fitting into the guide part 32 on the side of the monitor body 9 is formed at both ends of the guide plate 33. Further, a hole 34 is provided in the center of the guide plate 33, so that the shaft 31 is detachably and rotatably inserted into the hole 34.

According to this embodiment of the invention, the monitor body 9 can be set at a desired angle with respect to the channel of the airway adaptor 1, whereby the display portion 13 becomes readily observable at the time of measurement. FIG. 5 refers to a case where the channel of the airway adaptor 1 is situated in a direction perpendicular to the display surface of the display portion 13, whereas FIG. 6 refers to a case where it obliquely intersects the display surface thereof.

Figure 7:
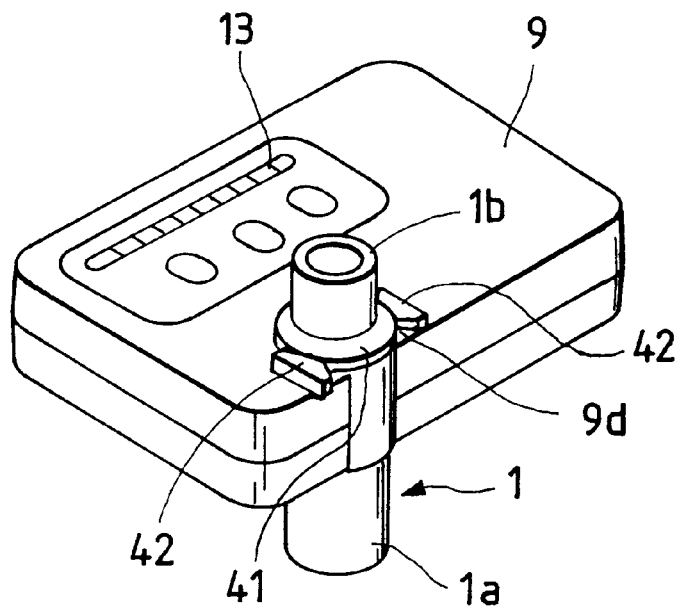
FIG. 7 is a perspective view of a second embodiment of the present invention.
Figure 8:
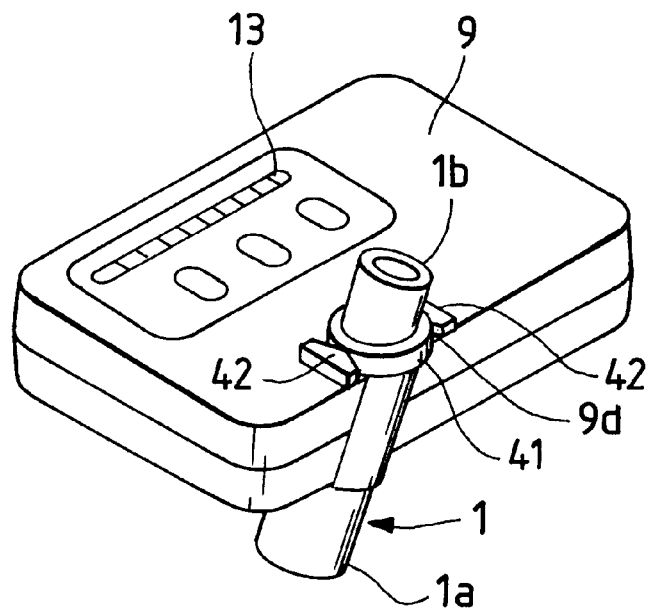
FIG. 8 is a perspective view of another capnometer embodying a second invention.

FIGS. 7 and 8 show another embodiment of a the invention. According to this embodiment of the invention, the detecting portion 2 is incorporated in the monitor body 9, and only the airway adaptor 1 is made detachable from the monitor body 9. A U-shaped cutaway portion 9d for receiving the airway adaptor 1 is formed on one side of the monitor body 9, and an integral retaining part 42 is provided on both sides of the cutaway portion 9d. Moreover, an elastic member 41 having pawls each resiliently engaging with the retaining parts 42 is provided on the outer periphery of the airway adaptor 1 and when the airway adaptor 1 is fitted to the monitor body 9, the pawls of the elastic member 41 engage with the respective retaining parts 42, so that the elastic member 41 is held in position.

The optical axis of the detecting portion 2 contained in the monitor body 9 as shown in FIG. 2 is set perpendicular to the channel of the airway adaptor 1. According to the embodiment of the present invention shown in FIG. 7, the channel of the airway adaptor 1 is set perpendicular to the display surface of the display portion 13 of the monitor body 9, whereas according to the embodiment of the present invention shown in FIG. 8, the channel thereof obliquely intersects the display surface thereof.

Figure 9:
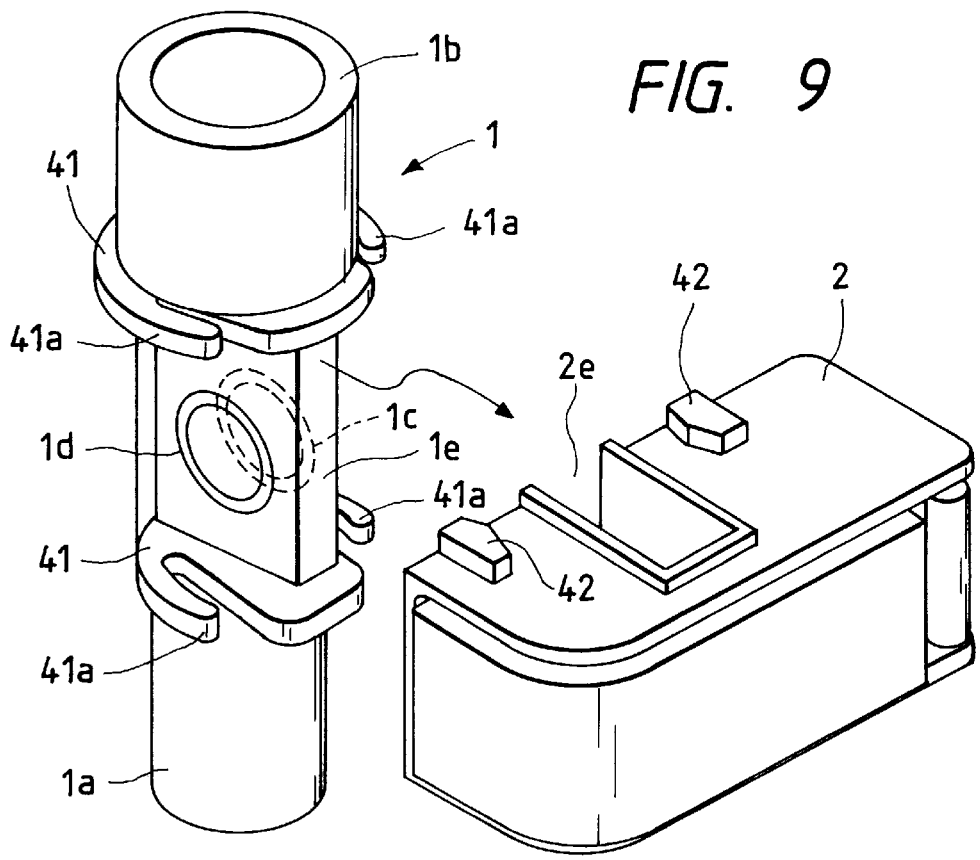
FIG. 9 is a perspective view of an airway adaptor detaching mechanism of a third embodiment of the present invention.

FIG. 9 shows an airway adapter detaching mechanism embodying the present invention. In FIG. 9, like reference characters designate like or corresponding parts of the prior art example shown in FIGS. 12, 13 and the description thereof will be omitted. As shown in FIG. 9, each elastic member 41 having pawls is formed of plastics and integral with the airway adaptor 1, and the elastic members 41 are provided at the respective connections between the one cylindrical end 1a and the intermediate portion 1e of the airway adaptor 1 square in cross section and between the other cylindrical end 1b and the intermediate portion 1e thereof. The elastic members 41 are set perpendicular to the axial direction of the airway adaptor, and part of the elastic member 41 is cut to form the pawls. In other words, the bilateral pairs of pawls 41a are projected from the outer peripheries of both ends 1a, 1b, respectively. Moreover, the space between the vertical pairs of elastic members 41 is set equal to the thickness of the detecting portion 2.

On the other hand, the retaining members 42 integral with both the surface and undersurface of the detecting portion 2 are formed with a predetermined space left therebetween on both sides of the end portion of a cutaway portion 2e into which the airway adaptor 1 formed in the detecting portion 2 is fitted. Moreover, the faces of the retaining members 42 are shaped like an inverted V, the inverted V-shaped portions facing each other.

Figure 10:
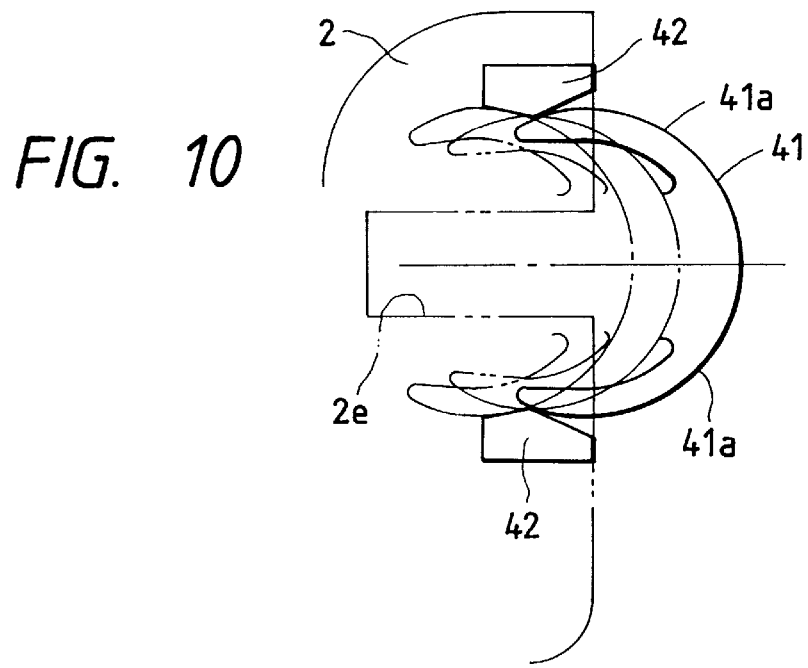
FIG. 10 is a top view showing a state in which the detecting portion of FIG. 9 has been fitted to the monitor body.

The function of this embodiment of the invention will subsequently be described by reference to FIG. 10. The airway adaptor 1 is manually held so as to fit the intermediate portion 1e into the cutaway portion 2e of the detecting portion 2. First, the leading ends of the pawls 41a of the elastic members 41 abut against the respective inverted V-shaped portions as shown by a solid line. When the airway adaptor 1 is forced into the cutaway portion 2e, the pawls 41a are pushed by the inverted V-shaped portions of the retaining members 42 as shown by a dashed line and undergo elastic inward deformation. When the airway adaptor 1 is actually forced into the cutaway portion 2e, the pawls 41a climb over the respective inverted V-shaped portions of the V-shaped members 42 as shown by a two-dot chain line, undergo deformation outward due to elastic force and abut against the inner tilted faces of the retaining members 42, whereby the airway adaptor 1 is held in position.

FIG. 2 shows a state in which the detecting portion 2 fitted with the airway adaptor 1 has been detachably fitted to the monitor body 9. In this case, the adjoining two sides of the detecting portion 2 are made arcuate and the monitor body 9 is provided with the arcuate cutaway portion 9a with which the detecting portion 2 mates.

According to this embodiment of the invention, the elastic members 41, each of which has the pawls with the predetermined space left therebetween, are provided on the outer periphery of the airway adaptor 1 and used to retain the airway adaptor 1 by making the elastic members 41 engage with the retaining parts 42 of the detecting portion 2, so that the airway adaptor 1 can be positioned accurately three-dimensionally with respect to the detecting portion 2. Moreover, the direction in which the elastic members 41 press the retaining parts 42 can be made different from the optical axis by properly setting the angle of the inverted V-shaped tilting portions of the retaining parts 42, whereby it is possible to minimize any bad influence resulting from increasing the space between a light source 3 and a light receiving portion 7. Further, the elastic members 41 and the retaining parts 42 can be made integral with the airway adaptor 1 and the detecting portion 2, respectively. Thus the number of parts can be decreased, whereas the construction of the capnometer can also be simplified.

Although a description has been given of a case where the two pairs of elastic members 41 for holding the detecting portion 2 therebetween according to the above embodiment of the invention, only one pair of elastic members 41 may be arranged for use. Further, only one elastic member 41a out of the elastic members 41 in pair may be arranged for use. Further, the retaining parts 42 are not limited to the inverted V-shape but may be round bars, for example.

Figure 11:
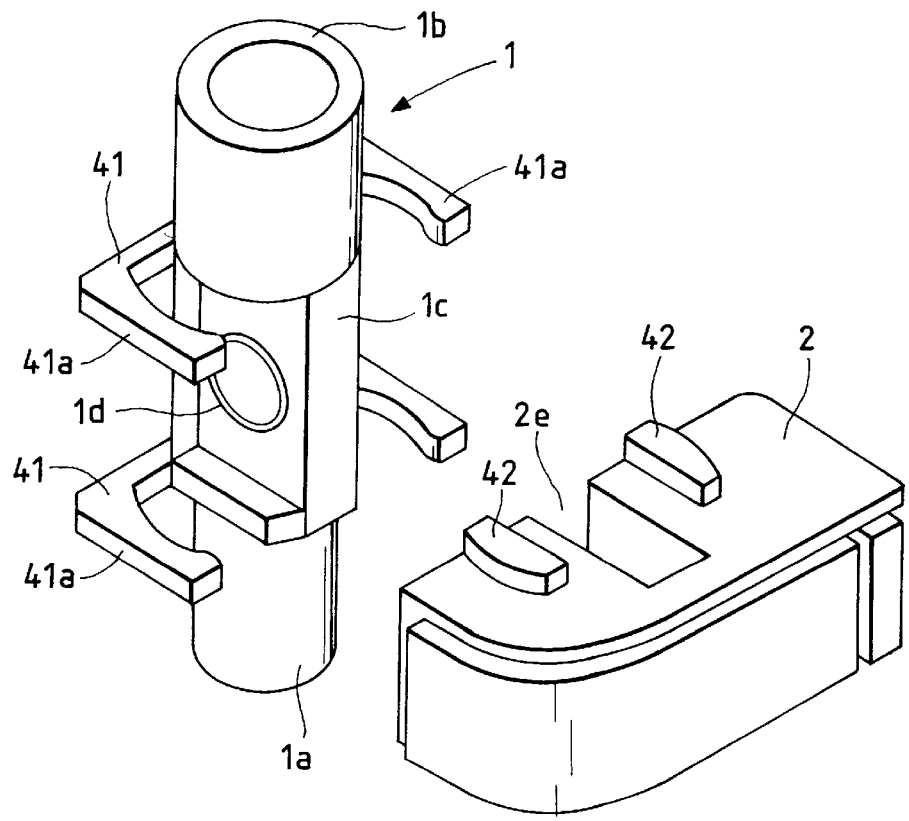
FIG. 11 is a perspective view of another airway adaptor detaching mechanism for a modified embodiment of the third invention.

Although a description has been given of a case where the elastic members 41 are pressed inward by the retaining parts 42 to undergo elastic deformation by way of example according to the above embodiment of the invention, the retaining parts 42 may be situated inside the elastic members 41 as shown in FIG. 11, so that they are forced to expand outward.

The retaining part may fixedly be provided on the side of the airway adaptor 1, whereas the elastic member may be provided on the side of the detecting portion 2. However, it is preferred to install the elastic member on the side of the airway adaptor 1 when the fatigue of such an elastic member is taken into consideration.

According to this embodiment of the invention, the same effect is achievable. Although the thermopile has been used as a heat detecting element according to the above embodiment of the invention, the same object with the same effect is also achievable by means of a thermistor bolometer.

As set forth above, the capnometer equipped with the compact, lightweight detecting portion having the thermopile as an infrared radiation detector according to the present invention is capable of measuring the concentration of respiratory carbon dioxide gas by making the detecting portion integral with the monitor body so that the channel of the airway adaptor intersects the display surface of the monitor body.

Consequently, it is possible to look the display portion for displaying the concentration of carbon dioxide while the patient's condition and complexion are watched.

Moreover, the elastic members 41 which have the pawls projected from the outer periphery of the airway adaptor through which the respiratory gas passes and which are integral with the airway adaptor, whereas the retaining parts are disposed so as to retain the elastic members situated close to the cutaway portion of the detecting portion into which the airway adaptor is fitted, whereby the airway adaptor can be retained in position in the detecting portion simply and accurately.

What is claimed is:

1. A capnometer comprising:

an airway adaptor for passing respiratory gas therethrough;

a detecting portion having a light source for irradiating infrared radiation and an infrared radiation detector for detecting the infrared radiation that has passed through the respiratory gas;

a detaching mechanism for detachably mounting said airway adaptor to said detecting portion, a monitor body, having a display surface for indicating the concentration of a respiratory carbon dioxide gas, for measuring the concentration of respiratory carbon dioxide gas by receiving a signal from said detecting portion, wherein said detecting portion is mounted onto said monitor body forming one unit, and wherein an angle is defined between a channel of said airway adaptor and said display surface of said monitor body while said airway adaptor is mounted to said detecting portion.

2. The capnometer as claimed in claim 1, wherein said detecting portion is detachable from said monitor body.

3. The capnometer as claimed in claim 1, wherein said detaching mechanism comprises:

an elastic member having at least one bilateral pair of pawl, said elastic member being integral with an outer periphery of said airway adaptor, and at least one pair of retaining parts provided near a cutaway portion into which said airway adapter is fitted and so arranged in said detecting portion as to retain said elastic member, wherein said pawls are pushed undergoing elastic inward deformation by said retaining parts, and then undergoing elastic outward deformation after clamping over said retaining parts due to elastic force when said airway adaptor is inserted into said detecting portion.

4. The capnometer as claimed in claim 3, wherein each of said pawls of said elastic member is arcuate in shape forming an arcuate pawl, and wherein each of said retaining parts is arranged to receive said arcuate pawl.

5. The capnometer as claimed in claim 4, wherein each of said retaining parts comprises a convex shape to receive said arcuate pawl.

6. The capnometer as claimed in claim 1, wherein said detaching mechanism comprises:

an elastic member having at least one bilateral pair of pawls, said elastic member being integral with an outer periphery of said airway adaptor, and at least one pair of retaining parts provided near a cutaway portion into which said airway adaptor formed in said detecting portion is fitted and so arranged in said detecting portion as to retain said elastic member;

wherein said pawls are pushed undergoing elastic outward deformation by said retaining parts, and then undergoing elastic inward deformation after clamping over said retaining parts due to elastic force when said airway adaptor is inserted into said detecting portion.

7. The capnometer as claimed in claim 6, wherein each of said pawls of said elastic member is arcuate in shape forming an arcuate pawl, and wherein each of said retaining parts is arranged to receive said arcuate pawl.

8. The capnometer as claimed in claim 7, wherein each of said retaining parts comprises a convex shape to receive said arcuate pawl.

9. The capnometer as claimed in claim 1, wherein said detecting portion is rotatable with respect to said monitor body.

10. The capnometer as claimed in claim 1, wherein said angle is approximately a right angle.

11. The capnometer as claimed in claim 1, wherein said infrared radiation detector comprises thermal energy detecting elements.

12. The capnometer as claimed in claim 1, wherein said infrared radiation detector comprises thermopile.

13. A capnometer comprising:

an airway adaptor for passing respiratory gas therethrough;

a detecting portion having a light source for irradiating infrared radiation and an infrared radiation detector for detecting the infrared radiation that has passed through the respiratory gas;

a detaching mechanism for detachably mounting said airway adaptor to said detecting portion, wherein said detaching mechanism comprises:

an elastic member having at least one bilateral pair of pawls, said elastic member being integral with an outer periphery of said airway adaptor, and at least one pair of retaining parts provided near a cutaway portion into which said airway adaptor formed in said detecting portion is fitted and so arranged in said detecting portion as to retain said elastic member;

wherein said pawls are pushed undergoing elastic inward deformation by said retaining parts, and then undergoing elastic outward deformation after clamping over said retaining parts due to elastic force when said airway adaptor is inserted into said detecting portion.

14. The capnometer as claimed in claim 13, wherein each of said pawls of said elastic member is arcuate in shape forming an arcuate pawl, and wherein each of said retaining parts is arranged to receive said arcuate pawl.

15. The capnometer as claimed in claim 14, wherein each of said retaining parts comprises a convex shape to receive said arcuate pawl.

16. A capnometer comprising:

an airway adaptor for passing respiratory gas therethrough;

a detecting portion having a light source for irradiating infrared radiation and an infrared radiation detector for detecting the infrared radiation that has passed through the respiratory gas;

a detaching mechanism for detachably mounting said airway adaptor to said detecting portion, wherein said detaching mechanism comprises:

an elastic member having at least one bilateral pair of pawls, said elastic member being integral with an outer periphery of said airway adaptor, and at least one pair of retaining parts provided near a cutaway portion into which said airway adaptor formed in said detecting portion is fitted and so arranged in said detecting portion as to retain said elastic member;

wherein said pawls are pushed undergoing elastic outward deformation by said retaining parts, and then undergoing elastic inward deformation after clamping over said retaining parts due to elastic force when said airway adaptor is inserted into said detecting portion.

17. The capnometer as claimed in claim 16, wherein each of said pawls of said elastic member is arcuate in shape forming an arcuate pawl, and wherein each of said retaining parts is arranged to receive said arcuate pawl.

18. The capnometer as claimed in claim 17, wherein each of said retaining parts comprises a convex shape to receive said arcuate pawl.

\* \* \* \* \*